(12) United States Patent
Hanakawa et al.

(10) Patent No.: US 9,157,107 B2
(45) Date of Patent: *Oct. 13, 2015

(54) METHOD OF PRODUCING COMPOUND ORIGINATING FROM POLYSACCHARIDE-BASED BIO-MASS

(71) Applicant: Toray Industries, Inc., Tokyo (JP)

(72) Inventors: Masayuki Hanakawa, Shiga (JP); Shinichi Minegishi, Shiga (JP); Hiroyuki Kurihara, Kanagawa (JP)

(73) Assignee: Toray Industries, Inc. (JP)

( * ) Notice: Subject to any disclaimer, the term of this patent is extended or adjusted under 35 U.S.C. 154(b) by 125 days.

This patent is subject to a terminal disclaimer.

(21) Appl. No.: 13/916,190

(22) Filed: Jun. 12, 2013

(65) Prior Publication Data

US 2013/0273608 A1    Oct. 17, 2013

Related U.S. Application Data

(62) Division of application No. 12/920,128, filed as application No. PCT/JP2009/053629 on Feb. 27, 2009, now Pat. No. 8,497,091.

(30) Foreign Application Priority Data

Mar. 5, 2008  (JP) ................. 2008-054472

(51) Int. Cl.

| | | |
|---|---|---|
| C12P 1/00 | (2006.01) | |
| C12P 7/06 | (2006.01) | |
| C12N 1/00 | (2006.01) | |
| B01D 71/00 | (2006.01) | |
| C12P 19/40 | (2006.01) | |
| C12P 7/04 | (2006.01) | |
| C12P 19/04 | (2006.01) | |
| C12P 19/14 | (2006.01) | |
| C12P 7/16 | (2006.01) | |
| C12P 7/56 | (2006.01) | |
| C12P 13/00 | (2006.01) | |

(52) U.S. Cl.
 CPC . *C12P 19/40* (2013.01); *C12P 7/04* (2013.01); *C12P 7/06* (2013.01); *C12P 7/16* (2013.01); *C12P 7/56* (2013.01); *C12P 13/001* (2013.01); *C12P 19/04* (2013.01); *C12P 19/14* (2013.01); *Y02E 50/16* (2013.01); *Y02E 50/17* (2013.01)

(58) Field of Classification Search
 CPC .......... B01D 1/00; B01D 23/00; B01D 45/00; B01D 61/00; B01D 2101/00; C08B 1/00; C12N 1/00; C12N 2303/00; C12N 2310/00; C12N 2700/00; C12N 2710/00; C12P 1/00; C12P 2201/00; C12P 2203/00; C13B 5/00; C13K 1/00
 USPC ..................... 435/41, 161, 243, 942; 210/634
 See application file for complete search history.

(56) References Cited

U.S. PATENT DOCUMENTS

| | | | |
|---|---|---|---|
| 4,857,363 | A | 8/1989 | Sasaki et al. |
| 7,077,953 | B2 | 7/2006 | Ranney |
| 2006/0016751 | A1 | 1/2006 | Ali et al. |
| 2006/0237361 | A1 | 10/2006 | Dudziak et al. |

FOREIGN PATENT DOCUMENTS

| | | |
|---|---|---|
| CN | 1594339 | 3/2005 |
| EP | 2 371 973 | 10/2011 |
| JP | 62-201606 | 9/1987 |
| JP | 5-096140 | 4/1993 |
| JP | 2004-169243 A | 6/2004 |
| JP | 2004-187650 | 7/2004 |
| JP | 2005-177741 | 7/2005 |
| JP | 2005-270056 | 10/2005 |
| JP | 2006-087350 | 4/2006 |
| JP | 2007-151433 | 6/2007 |
| JP | 2008-054472 | 3/2008 |
| JP | 2008-313167 | 12/2008 |

OTHER PUBLICATIONS

Murthy, G.S. et al., "Concentration of Xylose Reaction Liquor by Nanofiltration for the Production of Xylitol Sugar Alcohol," *Separation and Purification Technology*, 2005, vol. 44, pp. 221-228.
Sakai, S. et al., "Effect of Lignocellulose-Derived Inhibitors on Growth of and Ethanol Production by Growth-Arrested *Corynebacterium glutamicum* R," *Applied and Environmental Microbiology*, Apr. 2007, pp. 2349-2353.
Chosakai, K., *Membrane Filtration Techniques* . . . , 2006, pp. 47-55.
Kim, S. et al., "Effect of pH on the Rejection of Inorganic salts and Organic Compound Using Nanofiltration Membrane," *Korean J. Chem. Eng.*, 2006, vol. 23, No. 1, pp. 28-29.

(Continued)

*Primary Examiner* — Maria Leavitt
(74) *Attorney, Agent, or Firm* — DLA Piper LLP (US)

(57) ABSTRACT

A method of producing a compound originating from a polysaccharide-based biomass includes at least one of a saccharification step that produces a sugar solution containing a monosaccharide and/or an oligosaccharide from a product obtainable by hydrolyzing the polysaccharide-based biomass; a fermentation step that ferments the sugar solution containing the monosaccharide and/or oligosaccharide originating from the polysaccharide-based biomass; and a treatment that removes a fermentation inhibitor with the use of a separation membrane having a glucose removal rate and an isopropyl alcohol removal rate which simultaneously satisfy the following relationships (I) and (II) when a 500 ppm aqueous glucose solution at pH 6.5 at 25° C. and a 500 ppm aqueous isopropyl alcohol solution at pH 6.5 at 25° C. are respectively permeated through the membrane at an operation pressure of 0.5 MPa, prior to the saccharification step and/or in the step prior to the fermentation step:

Glucose removal rate≥80%    (I)

Glucose removal rate−Isopropyl alcohol removal rate≥20%    (II).

12 Claims, No Drawings

(56) References Cited

OTHER PUBLICATIONS

Yuan, Q. et al., "Pilot-Plant Production of Xylo-Oligosaccharides from Corncob by Steaming, Enzymatic Hydrolysis and Nanofiltration," *Journal of Chemical Technology and Biotechnology*, 2004, vol. 79, pp. 1073-1079.

Boussu, K. et al., "Physico-Chemical Characterization of Nanofiltration Membranes," *ChemPhysChem*, 2007, vol. 8, pp. 370-379.

Kim, H-A. et al., "Comparison of Initial Filtration Resistance by Pretreatment Processes in the Nanofiltration for drinking Water Treatment," *Separation and Purification Technology*, 2007, vol. 56, pp. 354-362.

"Useful Membrane Filtration Technology," partial publication in Japanese with handwritten English translations on p. 2.

"Technologies Utilizing Biomass Energy," reviewed by Yukawa, Hideaki, *CMC Publishing, Inc.*, 2006, pp. 155-160 and 6 pages of partial English translation.

"Lectures on Experimental Chemistry, 4th Edition," edited by the Chemical Society of Japan, *Maruzen Corp.*, 1992, vol. 14, pp. 485-488 and 3 pages of partial English translation.

Kirkegaard, P. et al., "Positronfit: A Versatile Program for Analysing Positron Lifetime Spectra," *Computer Physics Communications*, vol. 3, 1972, pp. 240-255.

Maddox, I.S. et al., "Production of n-Butanol by Fermentation of Wood Hydrolysate," *Biotechnology Letters*, vol. 5, No. 3, 1983, pp. 175-178.

Ohlson, I. et al., "Evaluation of UF and RO in a cellulose Saccharification Process," *Desalination*, vol. 51, 1984, pp. 93-101.

Nakanishi, H. et al., "Positronium Formation at Free-volume Sites in the Amorphous Regions of Semicrystalline PEEK," *Journal of Polymer Science: Part B: Polymer Physics*, vol. 27, 1989, pp. 1419-1424.

Mänttäri, M. et al., "Fouling Effects of Polysaccharides and Humic Acid in Nanofiltration," *Journal of Membrane Science*, vol. 165, 2000, pp. 1-17.

Suzuki, R. et al., "A Positron Lifetime Spectroscopy Apparatus for Surface and Near-surface Positronium Experiments," *Radiation Physics and Chemistry*, vol. 58, 2000, pp. 603-606.

Banvolgyi, S. et al., "Concentration of Red Wine by Nanofiltration," *Desalination*, vol. 198, 2006, pp. 8-15.

Inoue, T., "Super Ultralow Pressure Nanofiltration (NF) Membrane" *Bunri Gijutsu*, 2001, vol. 31, pp. 322-325, English translation.

Klinke et al., "Inhibition of Ethanol-Producing Yeast and Bacteria by Degradation Products Produced during Pre-Treatment of Biomass," *Appl. Microbiol. Biotechnol.*, Nov. 2004, vol. 66, No. 1, pp. 10-26.

Shigeki Sawada, "Membrane Filtration Techniques Helpful for an the job (Genba de yakudatsu maku-rokagiju-tsu)", Kogyo Chosakai Publishing Co., Ltd., Jul. 10, 2006, with brief English summary.

METHOD OF PRODUCING COMPOUND ORIGINATING FROM POLYSACCHARIDE-BASED BIO-MASS

CROSS REFERENCE TO RELATED APPLICATION

This application is a divisional of U.S. application Ser. No. 12/920,128, filed on Aug. 30, 2010, now issued as U.S. Pat. No. 8,497,091, which is a 371 of PCT/JP2009/053629 filed Feb. 27, 2009, which claims priority to Japanese Application No. 2008-054472 filed Mar. 5, 2008.

TECHNICAL FIELD

This disclosure relates to a highly efficient method of producing a compound originating from a polysaccharide-based biomass, the method including providing a treatment for removing a fermentation inhibitor with the use of a separation membrane in the step prior to the saccharification step and/or in the step prior to the fermentation step, in at least one of the following steps, that is, a step for producing a monosaccharide and/or an oligosaccharide of a pentose and/or a hexose by using a polysaccharide-based biomass as a starting material, and a step for converting the monosaccharide and/or oligosaccharide thus obtained into a chemical via fermentation.

BACKGROUND

The twentieth century, which is known as the era of mass consumption and mass disposal, has come to an end, and in the twenty-first century where establishment of an environmentally friendly society is demanded, as the problem of depletion of fossil resources and the problem of global warming are becoming more serious, promotion of the utilization of biomass resources, which are recyclable resources, is under expectation.

Currently, among the biomass resources, production of bioethanol using sugar cane or corn as a starting material is in active progress in the United States, Brazil and the like. This is because sugar cane or corn contains a rich content of sucrose or starch, and accordingly, it is easy to prepare a sugar solution therefrom for fermentation. However, sugar cane and corn are originally foodstuffs, and when these are used as starting materials, there is a serious problem that a competition occurs between the usage as the starting material and the usage as foodstuffs or feedstock, causing an increase in the starting material price. Thus, development of a technology to use a non-edible biomass as a starting material is under way.

Examples of the non-edible biomass include cellulose that is present most abundantly on Earth, and most of cellulose exists in the form of a polysaccharide-based biomass which is a complex of cellulose with lignin or a hemicellulose, which is an aromatic polymer. A technology of producing a monosaccharide or an oligosaccharide of a pentose or a hexose from cellulose or hemicelluloses in a polysaccharide-based biomass, fermenting the obtained monosaccharide or oligosaccharide, and converting the fermentation product to various compounds originating from a polysaccharide-based biomass, such as ethanol or lactic acid, is attracting public attention. However, as described in Technologies Utilizing Biomass Energy, reviewed by Yukawa, Hideaki, CMC Publishing, Inc, (2006), a polysaccharide-based biomass is a complicated construct of cellulose, hemicelluloses and lignin, and cellulose or hemicelluloses are protected by lignin from being subjected to biodegradation, so that the composition ratios vary in a wide range depending on the regional and seasonal conditions and the starting material. For this reason, it is not easy to selectively pick out only a monosaccharide or an oligosaccharide of a pentose or a hexose.

Investigations have hitherto been made on a pretreatment method of destroying or softening the protective walls of lignin by treating a polysaccharide-based biomass using an acid, an alkali, an enzyme, subcritical water (supercritical water) or the like, and recovering a liquid or solid containing a monosaccharide or an oligosaccharide of a pentose or a hexose. For example, since a treatment based on subcritical water (supercritical water) has a short treatment time, and does not require a mineral acid or the like, that is, does not require a neutralization treatment, the treatment is advantageous from an environmental aspect such that a side product such as plaster is not generated. Thus, this treatment is attracting attention as a next-generation treatment method of environmentally conscious type. However, as described in JP-A-2005-270056, since subcritical water (supercritical water) is highly reactive, there are difficulties in controlling the reactivity, and various fermentation inhibitors such as furfural and 5-hydroxymethylfurfural, which are overdegradation products of sugars, as well as vanillin and guaiacol, which are lignin-derived aromatic compounds, are also generated at the same time, so that the treatment product cannot be directly used in the fermentation step. Furthermore, according to the pretreatment conditions, the concentration of the obtainable monosaccharide or oligosaccharide of a pentose or a hexose may be low, and in this case, it is necessary to carry out simple concentration of the monosaccharide or oligosaccharide to about several-fold to ten-fold before supplying the monosaccharide or oligosaccharide to the fermentation process. At this time, while the monosaccharide or oligosaccharide of a pentose or a hexose is concentrated, the fermentation inhibitors are also concentrated at the same time, so that it is difficult to use the concentrate in the fermentation process.

In regard to such problems, investigations are being made on the removal of fermentation inhibitors. For instance, Biotechnology Letters, Vol. 5, No, 3, pp. 175-178 (1983) discloses a method of removing a fermentation inhibitor through adsorption to activated carbon. However, this method has a problem that since the activated carbon adsorbs not only fermentation inhibitors but also monosaccharides or oligosaccharides of pentoses or hexoses, the yield of the monosaccharides or oligosaccharides of pentoses or hexoses is decreased.

JP-A-2005-270056 discloses a method of removing fermentation inhibitors through adsorption to wood-based carbon, and in this method, since fermentation inhibitors can be selectively adsorbed and removed, a monosaccharide or an oligosaccharide of a pentose or a hexose can be obtained with a good yield. However, since the removal mechanism involves adsorption, if the adsorption capacity is saturated, the fermentation inhibitors run off and contaminate the apparatuses, pipes and the like in the subsequent steps. Unless the fermentation reaction is carried out accurately, high quality products cannot be obtained, and especially in the case of carrying out the production by continuously operating the apparatuses while continuously supplying the starting materials, a method of stably and certainly removing fermentation inhibitors is desired, because the occurrence of contamination of apparatuses, pipes and the like brings on an increase in the cost and a decrease in the product quality. Furthermore, in the case of using a starting material having a low concentration of a monosaccharide or oligosaccharide of a pentose or a hexose, a method capable of reducing two steps, namely, a step for the concentration of a monosaccharide or an oligosaccharide of a pentose or a hexose and a step for the removal of fermentation inhibitors, into one step, or reducing the burden of the concentration step, is desired from the viewpoint of reducing the cost and enhancing the product quality.

On the other hand, in the case of using construction waste materials such as plywood as a polysaccharide-based biomass, acetic acid, formic acid and the like originating from the adhesive contained in the plywood act as fermentation inhibitors. There, JP-A-2004-187650 discloses a method of removing volatile fermentation inhibitors such as acetic acid and formic acid by distillation. This method is barely effective only when the non-volatile fermentation inhibitors that cannot be removed by distillation are present at a concentration that does not have adverse effects on the fermentation process, and it is difficult to apply the method when a polysaccharide-based biomass having a broad composition range is used as a starting material.

It could therefore be helpful to provide a method of producing a compound originating from a polysaccharide biomass by stably and certainly removing fermentation inhibitors that serve as an obstacle to reduce the burden of and to promote streamlining of at least one of the following steps, that is, a step for producing a monosaccharide and/or an oligosaccharide of a pentose and/or a hexose using a polysaccharide-based biomass having a broad composition range as a starting material, and a step for converting the monosaccharide and/or oligosaccharide thus obtained into a chemical via fermentation.

SUMMARY

We thus provide:

1) A method of producing a compound originating from a polysaccharide-based biomass, the method including at least one of a saccharification step for producing a sugar solution containing a monosaccharide and/or an oligosaccharide from a product obtainable by hydrolyzing the polysaccharide-based biomass, and a fermentation step for fermenting the sugar solution containing the monosaccharide and/or oligosaccharide originating from the polysaccharide-based biomass, wherein a treatment for removing a fermentation inhibitor with the use of a separation membrane having a glucose removal rate and an isopropyl alcohol removal rate which simultaneously satisfy the following relationships (I) and (II) when a 500 ppm aqueous glucose solution at pH 6.5 at 25° C. and a 500 ppm aqueous isopropyl alcohol solution at pH 6.5 at 25° C. are respectively permeated through the membrane at an operation pressure of 0.5 MPa, is carried out in the step prior to the saccharification step and/or in the step prior to the fermentation step:

Glucose removal rate≥80%　　　(I)

Glucose removal rate−Isopropyl alcohol removal rate≥20%.　　　(II)

2) The method of producing a compound originating from a polysaccharide-based biomass as set forth in item 1), wherein the treatment for removing a fermentation inhibitor with the use of a separation membrane allows removal of the fermentation inhibitor and concurrent concentration of cellulose, a hemicellulose, a monosaccharide and/or an oligosaccharide.

3) The method of producing a compound originating from a polysaccharide-based biomass as set forth in item 1), wherein a treatment for concentrating the compound with the use of a reverse osmosis membrane is performed after the treatment for removing a fermentation inhibitor with the use of a separation membrane, and before the fermentation step.

4) The method of producing a compound originating from a polysaccharide-based biomass as set forth in item 1), wherein the treatment for removing a fermentation inhibitor with the use of a separation membrane is carried out until the content of the fermentation inhibitor in the sugar solution obtainable immediately before the fermentation step reaches 500 ppm or less.

5) The method of producing a compound originating from a polysaccharide-based biomass as set forth in item 1), wherein the separation membrane has pores having an average pore radius as measured by a positron annihilation lifetime spectroscopy, of from 0.8 nm to 4.0 nm.

6) The method of producing a compound originating from a polysaccharide-based biomass as set forth in item 5), wherein the average pore radius is from 2.5 nm to 4.0 nm.

There is provided a method of producing a compound originating from a polysaccharide biomass, in which method a treatment for removing, with the use of a separation membrane, a fermentation inhibitor which serves as an obstacle in at least one of the following steps, that is, a step for producing a monosaccharide and/or an oligosaccharide of a pentose and/or a hexose using a polysaccharide-based biomass as a starting material, and a step for converting the monosaccharide and/or oligosaccharide thus obtained into a chemical via fermentation, is performed in the step prior to the saccharification step and/or in the step prior to the fermentation step. The separation membrane is capable of continuously removing fermentation inhibitors and is capable of controlling the water quality when separation membranes are selected and connected as necessary. Furthermore, the method of supplying raw water to the separation membrane can also be freely designed, such as to include varying the recovery rate or circulating a part of the raw water. Therefore, it is made possible to remove fermentation inhibitors to a concentration that does not adversely affect the subsequent processes, even when a polysaccharide-based biomass having a broad composition range is used as a starting material.

DETAILED DESCRIPTION

The polysaccharide-based biomass that is a subject to be treated by the method mainly contains cellulose, hemicellulose and lignin, and examples thereof include agroforestry resources, agroforestry waste materials and agroforestry processed products such as softwood, hardwood, construction waste materials, forest wood residues, pruned wood waste, rice straw, rice husk, wheat straw, wood chip, wood fiber, chemical pulps, used paper and plywood. In addition, materials containing less or no lignin, for example, sucrose-containing resources such as sugar cane and sugar beet, and starch-containing resources such as corn and sweet potato, may also be used as the subject to be treated by the method as long as the materials contain or produce fermentation inhibitors, representative examples of which include overdegradation products of sugars. These polysaccharide-based biomasses may be used singly or may be used in a mixture.

Hemicelluloses have sugars called pentoses such as xylose, each having five carbon atoms as constituent units, sugars called hexoses such as mannose, arabinose and galacturonic acid, each having six carbon atoms as constituent units, and complex polysaccharides such as glucomannan and glucuronoxylan. Thus, when subjected to hydrolysis, hemicelluloses generate a monosaccharide of a pentose formed from five carbon atoms, an oligosaccharide of a pentose having a plural number of the monosaccharide linked together, a monosaccharide of a hexose formed from six carbon atoms, an oligosaccharide of the hexose having a plural number of the monosaccharide connected together, and an oligosaccharide having plural numbers of a monosaccharide of a pentose and a monosaccharide of a hexose linked together. Cellulose has six carbon atoms as constituent units, and thus when subjected to hydrolysis, cellulose generates a monosaccharide of a hexose formed from six carbon atoms, and an oligosaccharide of the hexose having a plural number of the monosaccharide linked together. In general, the composition ratio or the production amount of a monosaccharide and/or an oligosaccharide of a pentose and/or a hexose varies with the pretreatment method or the type of the agroforestry resource, agroforestry waste material or agroforestry processed product used as a starting material.

Various treatment flows for polysaccharide-based biomasses have been suggested, but the outline can be explained as follows. First, a polysaccharide-based biomass is treated by hydrolysis to remove or soften lignin, and is supplied to a pretreatment process for making extraction of cellulose or a hemicellulose easy. Subsequently, a saccharification process is carried out in which the cellulose and a hemicellulose thus obtained are further treated by hydrolysis, and a monosaccharide and/or an oligosaccharide of a pentose and/or a hexose is collected. The hydrolysis treatments in the pretreatment process and the saccharification process may be, for example, treatments making use of acid, alkali, enzyme, high temperature and high pressure (subcritical water, supercritical water) or the like, and these treatments can be used singly or in combination.

Furthermore, the pretreatment process and the saccharification process may be carried out each independently, or may be carried out concurrently. After the saccharification process, a fermentation process is carried out in which cellulose, a hemicellulose, a monosaccharide and/or an oligosaccharide of a pentose and/or a hexose are used as starting materials to convert them via fermentation into various compounds originating from a polysaccharide-based biomass, such as alcohols such as ethanol, butanol, 1,3-propanediol, 1,4-butanediol and glycerol; organic acids such as pyruvic acid, succinic acid, malic acid, itaconic acid, citric acid and lactic acid; nucleosides such as inosine and guanosine; nucleotides such as inosinic acid and guanylic acid; and diamine compounds such as cadaverine. When the compound thus obtained via fermentation is a monomer such as lactic acid, a polymerization process for converting the monomer into a polymer via polymerization may also be carried out. Finally, after the fermentation process or the polymerization process, a purification process is often carried out so as to enhance the quality of the resulting various compounds originating from a polysaccharide-based biomass.

As described above, in the pretreatment process or saccharification process, the polysaccharide-based biomass is subjected to a hydrolysis treatment according to a known method making use of acid, alkali, enzyme, high temperature and high pressure (subcritical water, super-critical water), or the like. The type or conditions of the hydrolysis treatment may be appropriately selected in view of the type of the polysaccharide-based biomass used as the starting material, and the cost for the overall process including fermentation, polymerization, purification and the like. The hydrolysis treatment may be carried out as single hydrolysis treatment, or may be carried out in combination of multiple hydrolysis treatments. For example, if an acid is used in the hydrolysis treatment in any of the pretreatment process and the saccharification process, the pretreatment process and the saccharification process may be carried out in the same step, or the respective processes may be carried out independently such that the pretreatment process is carried out under a relatively higher temperature, while the saccharification process is carried out at a relatively lower temperature. There may also be employed, for example, a method of carrying out a pretreatment process which is focused on the removal or softening of lignin with the use of subcritical water, and then subsequently carrying out a saccharification process which is focused on the production of a monosaccharide and/or an oligosaccharide of a pentose and/or a hexose from cellulose or a hemicellulose with the use of an enzyme.

From the polysaccharide-based biomass which has been subjected to a hydrolysis treatment in the pretreatment process, various side products are obtained in addition to the monosaccharide and/or oligosaccharide of a pentose and/or a hexose. If those side products are substances that do not adversely affect the enzymatic saccharification, fermentation and the like of the subsequent steps, the side products may be removed in any process such as a purification process for enhancing the product quality, and thus do not raise a serious problem. However, if the side products are fermentation inhibitors that have adverse effects, there arises a necessity to remove the side products in the steps prior to the enzymatic saccharification and fermentation, to an extent that the side products do not adversely affect the respective processes.

In general, a fermentation inhibitor is a substance that obstructs an enzymatic reaction or a fermentation reaction in a saccharification process making use of enzyme or in a fermentation process. Representative examples of the fermentation inhibitor include overdegradation products of sugars, lignin or lignin-derived aromatic compounds, and compounds originating from adhesives or coating materials. Among these, those compounds originating from artificial chemicals such as adhesives and coating materials can be avoided to some extent, by using naturally occurring polysaccharide-based biomasses that have not be subjected to those treatments. However, as long as a polysaccharide-based biomass is used as a starting material, it is difficult to avoid the generation of overdegradation products of sugars or lignin-derived aromatic compounds. When the fermentation inhibitors are insoluble solids such as lignin, and cellulose, hemicelluloses, monosaccharides and/or oligosaccharides of pentoses and/or hexoses are soluble, it may be possible to remove the fermentation inhibitors via conventional solid-liquid separation. However, if the fermentation inhibitors as well as the useful substances are all soluble, conventional solid-liquid separation cannot be applied, and therefore, the treatment method of removing a fermentation inhibitor with the use of a separation membrane as used in the present invention is applied with preference. That is, a fermentation inhibitor refers to a material which substantially forms a mixed solution with cellulose, a hemicellulose, a monosaccharide and/or an oligosaccharide of a pentose of a hexose, and is in a state of being inseparable or hardly separable through conventional solid-liquid separation. Examples of such a fermentation inhibitor include acetic acid, formic acid, levulinic acid, furfural and 5-hydroxymethylfurfural, which are overdegradation products of sugars, vanillin, acetovanillin and guaiacol, which are lignin-derived aromatic compounds.

The fermentation inhibitor concentration that inhibits an enzymatic reaction or a fermentation reaction may vary with the respective reactions, but is generally said to be a concentration of 500 to 1000 ppm or greater. Accordingly, it is preferable to remove the fermentation inhibitor to a concentration of 500 ppm or less, more preferable to remove to a concentration of 150 ppm or less, and most preferable to remove to 0 ppm (detection limit), before the fermentation inhibitor is supplied to a saccharification process making use of enzyme or a fermentation process. As the fermentation inhibitor concentration is removed more and more, the burden of the saccharification process making use of enzyme or the fermentation process is reduced, and thus more efficient operation of the saccharification process making use of enzyme or the fermentation process can be attempted. However, in practice, the cost required in the step for removing the fermentation inhibitor with the use of a separation membrane and the cost required in the processes for enzymatic saccharification, fermentation, polymerization, purification and the like in the subsequent steps are taken into consideration, and the fermentation inhibitor concentration that would give a minimum total cost is calculated.

A separation membrane is used to remove a fermentation inhibitor from a solution containing cellulose, a hemicellulose, a monosaccharide and/or an oligosaccharide of a pentose and/or a hexose, and the separation membrane is not particularly limited as long as it is capable of separating the fermentation inhibitor from cellulose, a hemicellulose, a monosaccharide and/or an oligosaccharide of a pentose and/or a hexose. The fermentation inhibitor that is to be removed may vary with the method of fermentation, but fermentation inhibitors are primarily low molecular weight compounds having a molecular weight of about 100 to 200, such as overdegradation products of sugars or lignin-derived aromatic compounds. On the other hand, the molecular weight of cellulose or a hemicellulose is generally as large as several hundreds to several ten thousands, while the molecular weight of a monosaccharide of a pentose and/or a hexose is about 100 to 200. For this reason, it was expected that it would be difficult in particular to separate between a fermentation inhibitor having a molecular weight of about 100 to 200 and a monosaccharide of a pentose and/or a hexose, on the basis of the membrane pore diameter, and the separation efficiency would be low.

However, we found that when a nanofiltration membrane is used as a separation membrane, particularly the glucose removal rate is high, and on the other hand, when a nanofiltration membrane having a large difference between the glucose removal rate and the isopropyl alcohol removal rate is used, separation of the two substances is achieved with high efficiency.

A nanofiltration membrane is a material called nanofiltration (nanofiltration membrane, NF membrane), and is a membrane which is generally defined as "a membrane allowing permeation of a monovalent ion and blocking a divalent ion." This is a membrane which is believed to have micropores having a size of about a few nanometers, and is mainly used for blocking microparticles, molecules, ions, salts and the like in water.

The mechanism for separation of a solute with the use of a nanofiltration membrane has not been satisfactorily elucidated even to the present, but it is said that separation is achieved by a combination of a separation mechanism based on charge repulsion, a separation mechanism based on the difference in the affinity to the separation membrane, a separation mechanism based on the membrane pore diameter, and the like. It is not very difficult to imagine that a separation membrane having a high removal rate for glucose, which is a kind of a hexose monosaccharide, would be able to concentrate a pentose or a hexose without permeating the sugar. However, it is a surprising fact that the tendency of separation between a fermentation inhibitor and the monosaccharides of a pentose and/or a hexose can be predicted by knowing the difference between the removal rates for glucose and isopropyl alcohol, which are non-chargeable organic substances. The reason is as follows. Fermentation inhibitors contain a lot of compounds having aromaticity, whether they be overdegradation products of sugars or lignin-derived aromatic compounds. In the separation between such compounds having aromaticity and those compounds that do not have aromaticity, such as pentoses or hexoses, the separation mechanism based on the difference in the affinity to the separation membrane works strongly. Therefore, it has been thought to be difficult to predict that those compounds can be easily separated, only by investigating the separation tendency of non-chargeable organic substances.

Although the reason of showing such a surprising tendency is not certainly known, it is believed that the separation mechanism based on the membrane pore diameter is predominant in the separation between the monosaccharides of pentoses and/or hexoses and the fermentation inhibitor with the use of a nanofiltration membrane of the separation membrane used. That is, it is thought that since a monosaccharide of a pentose and/or a hexose is highly hydrophilic, the monosaccharide molecules many water molecules along with themselves in water and have a large hydration radius. However, since a fermentation inhibitor has low hydrophilicity, the inhibitor molecules does not a hydration radius similar to that of a monosaccharide of a pentose and/or a hexose, and this difference in hydration radius has effects on the separation mechanism based on the membrane pore size, thereby separation being achieved.

It is preferable to use a nanofiltration membrane as a separation membrane. As the material for the nanofiltration membrane used, a polymeric material such as a cellulose ester-based polymer such as cellulose acetate, polyamide, polyester, polyimide or a vinyl polymer can be used. However, the membrane is not limited to a membrane constructed from a single kind of material, and may also be a membrane containing plural membrane materials. The membrane structure may be either an asymmetric membrane which has a dense layer on at least one surface of the membrane and has pores having a pore diameter that gradually increases from the dense layer toward the interior of the membrane or toward the other surface, or a composite membrane having, on the dense layer of the asymmetric membrane, a very thin functional layer formed from a different material. As the composite membrane, use can be made of, for example, a composite membrane that constitutes a nanofilter formed from a polyamide functional layer on a supporting film of polysulfone as the film material, as described in JP-A-62-201606.

Among these, a composite membrane having a functional layer formed from polyamide, which has high pressure resistance, high water permeability and high solute removal performance altogether and has an excellent potential, is preferred. For the composite membrane to be able to maintain durability against the operation pressure, high water permeability and blocking performance, a structure having a functional layer made of polyamide and retaining the functional layer on a support formed from a porous membrane or a non-woven cloth, is suitable. Furthermore, a suitable polyamide semipermeable membrane is a composite semipermeable membrane having a crosslinked polyamide functional layer which is obtainable by a polycondensation reaction between a polyfunctional amine and a polyfunctional acid halide, provided on a support.

In regard to a nanofiltration membrane having a functional layer made of polyamide, preferred examples of the carboxylic acid component of the monomer that constitutes the polyamide include aromatic carboxylic acids such as trimesic acid, benzophenonetetracarboxylic acid, trimellitic acid, pyrometic acid, isophthalic acid, terephthalic acid, naphthalenedicarboxylic acid, diphenylcarboxylic acid and pyridinecarboxylic acid. Upon the formation of a membrane, halides or anhydrides of these carboxylic acids are used with preference to increase the reactivity with the amine component that will be described below. However, if handlability such as solubility in solvent in particular is taken into consideration, halides of trimesic acid, isophthalic acid, terephthalic acid and mixtures of these acids are more preferred.

Preferred examples of the amine component for the monomer that constitutes the polyamide include primary diamines having aromatic rings, such as m-phenylenediamine, p-phenylenediamine, benzidine, methylenebisdianiline, 4,4'-diaminobiphenyl ether, dianisidine, 3,3',4-triaminobiphenyl ether, 3,3',4,4'-tetraminobiphenyl ether, 3,3'-dioxybenzidine, 1,8-naphthalenediamine, m(p)-monomethylphenylenediamine, 3,3'-monomethylamino-4,4'-diaminobiphenyl ether, 4,N,N'-(4-aminobenzoyl)-p(m)-phenylenediamine-2,2'-bis(4-aminophenylbenzoimidazole), 2,2'-bis(4-aminophenylbenzoxazole) and 2,2'-bis(4-aminophenylbenzothiazole); and secondary diamines such as piperazine, 2,5-dimethylpiperazine, piperidine and derivatives thereof. A nanofiltration membrane having a functional layer made of a crosslinked polyamide containing piperazine or piperidine as a monomer, has heat resistance and chemical resistance in addition to pressure resistance and durability, and thus is used with preference. A more preferred example is a polyamide containing the crosslinked piperazine polyamide the crosslinked piperidine polyamide as a main component, and a more preferred example is a polyamide containing the crosslinked piperazine polyamide as a main component. Examples of the nanofiltration membrane containing a crosslinked piperazine polyamide as a main component include those described in JP-A-62-201606, and a specific example may be a crosslinked polyamide nanofiltration (NF) membrane (UTC-60) manufactured by Toray Industries, Inc.

Furthermore, even in the method of forming an ultrathin film layer of a crosslinked polyamide on a supporting film containing polysulfone as a film material, and then treating the ultrathin film layer with an aqueous solution of a peroxymono compound or an aqueous solution of a peroxydisulfuric acid compound, as described in JP-A-5-96140, a nanofiltration membrane is obtainable by controlling the treatment conditions. The crosslinked polyamide can be produced from the carboxylic acid components and amine components mentioned above.

A nanofiltration membrane is also obtainable by bringing a polyamide film having a functional layer that contains a primary amino group, into contact under appropriate conditions, with a reagent that is capable of producing a diazonium salt or a derivative thereof by reacting with a primary amino group, as described in JP-A-2005-177741. To obtain a functional layer containing a primary amino group, among the amine components mentioned above, a primary diamine having an aromatic ring, such as m-phenylenediamine, p-phenylenediamine, benzidine, methylenebisdianiline, 4,4'-diaminobiphenyl ether, dianisidine, 3,3',4-triaminobiphenyl ether, 3,3',4,4'-tetraminobiphenyl ether, 3,3'-dioxybenzidine, 1,8-naphthalenediamine, m(p)-monomethylphenylenediamine, 3,3'-monomethylamino-4,4'-diaminobiphenyl ether, 4,N,N'-(4-amino-benzoyl)-p(m)-phenylenediamine-2,2'-bis(4-aminophenylbenzoimidazole), 2,2'-bis(4-aminophenylbenzoxazole), or 2,2'-bis(4-aminophenylbenzothiazole), may be used.

As a nanofiltration membrane that is preferable as the separation membrane, in particular, a nanofiltration membrane having a high glucose removal rate and having a large difference in the glucose removal rate and the isopropyl alcohol removal rate is preferred, because it is easier to separate between a monosaccharide of a pentose and/or a hexose and a fermentation inhibitor. Therefore, a nanofiltration membrane having a glucose removal rate of 80% or greater and a difference between the glucose removal rate and the isopropyl alcohol removal rate of 20% or greater is needed. It is more preferable that the glucose removal rate be 90% or greater, and it is even more preferable that the glucose removal rate be 95% or greater. Furthermore, it is more preferable that the difference between the glucose removal rate and the isopropyl alcohol removal rate be 30% or greater, and it is even more preferable that the glucose removal rate and the isopropyl alcohol removal rate be 50% or greater.

A nanofiltration membrane having a glucose removal rate of 80% or greater and a difference between the glucose removal rate and the isopropyl alcohol removal rate of 20% or greater is needed, but a nanofiltration membrane can be appropriately selected so that, after these conditions are satisfied, a recovery rate for cellulose, a hemicellulose, a monosaccharide and/or an oligosaccharide of a pentose and/or a hexose, and a recovery rate for a fermentation inhibitor may be obtained in view of the water quality of the liquid to be treated and the total costs. For example, when the concentration of the fermentation inhibitor is low and the concentration of the cellulose, hemicellulose, monosaccharide and/or oligosaccharide of a pentose and/or a hexose is high, it is preferable to give priority to the glucose removal rate over the difference between the glucose removal rate and the isopropyl alcohol removal rate, so that the outflow of the cellulose, hemicellulose, monosaccharide and/or oligosaccharide of a pentose and/or a hexose can be suppressed, and then the fermentation inhibitor can be removed. In this case, a glucose removal rate of the nanofiltration membrane of 95% or greater is preferred, a glucose removal rate of 98% or greater is more preferred, and a glucose removal rate of 99% or greater is even more preferred. On the other hand, a difference between the glucose removal rate and the isopropyl alcohol removal rate of the nanofiltration membrane of 25% or greater is preferred, and a difference between the glucose removal rate and the isopropyl alcohol removal rate of 30% or greater is more preferred. Furthermore, for example, when the concentration of the fermentation inhibitor is high and the concentration of the cellulose, hemicellulose, monosaccharide and/or oligosaccharide of a pentose and/or a hexose is low, it is preferable to give priority to the difference between the glucose removal rate and the isopropyl alcohol removal rate over the glucose removal rate, because the fermentation inhibitor can be removed in a short time. In this case, a difference between the glucose removal rate and the isopropyl alcohol removal rate of the nanofiltration membrane of 30% or greater is preferred, a difference between the glucose removal rate and the isopropyl alcohol removal rate of 50% or greater is more preferred, and a difference between the glucose removal rate and the isopropyl alcohol removal rate of 60% or greater is even more preferred. On the other hand, a glucose removal rate of the nanofiltration membrane of 90% or greater is preferred, and a glucose removal rate of 95% or greater is more preferred.

The glucose removal rate or the isopropyl alcohol removal rate is evaluated by using a 500 ppm aqueous glucose solution or a 500 ppm aqueous isopropyl alcohol solution at pH 6.5 at 25° C., permeating each of the solutions through a separation membrane at an operation pressure of 0.5 MPa, and comparing the concentrations of glucose or isopropyl alcohol in the permeation water and the source water. That is, calculation is performed by the following formula: glucose removal rate (%)=100×(1−(glucose concentration in permeation water/glucose concentration in source water)), and isopropyl alcohol removal rate (%)=100×(1−(isopropyl alcohol concentration in permeation water/isopropyl alcohol concentration in source water)).

For the nanofiltration membrane showing a glucose removal rate and an isopropyl alcohol removal rate in the range mentioned above, when the average pore radius of the separation functional layer of the membrane is measured by a positron annihilation lifetime spectroscopy, it was found that the average pore radius is from 0.8 nm to 4.0 nm. The separation functional layer of the nanofiltration membrane is a layer responsible for substantial separation of a solute in the nanofiltration membrane, and is generally located at the outermost layer or near the surface layer of the nanofiltration membrane.

The positron annihilation lifetime spectroscopy is a technique of measuring the time taken by a positron from the point of entrance into a sample to the point of annihilation (in the order of several hundred picoseconds to several ten nanoseconds), and non-invasively evaluating the data related to the size of pores of about 0.1 to 10 nm, the number density and the size distribution based on the annihilation lifetime. In regard to such an analysis method, the details are described in, for example, "Lectures on Experimental Chemistry, 4$^{th}$ Edition," Vol. 14, p. 485, edited by the Chemical Society of Japan, published by Maruzen Corp. (1992).

This technique is roughly classified into two types based on the type of the positron radiation source. One type is a $^{22}$Na method making use of a radioisotope ($^{22}$Na) as the positron radiation source, and is appropriate for an evaluation of pores in resins, powders, fibers, liquids and the like. The other type is a positron beam method making use of a positron beam emitted from an electron linear accelerator, as the positron radiation source, and enables an evaluation of pores of thin films having a thickness of several hundred nanometers formed on various bases. Particularly, in the latter positron beam method, even when a nanofiltration membrane is used as a sample to be measured, the functional layer of the nanofiltration membrane can be measured only by bringing the membrane to a dry state, and there is no need in particular to perform processing such as separation of the separation functional layer from the nanofiltration membrane. Therefore, the positron beam method is more preferred as a method for analysis of the separation functional layer of a nanofiltration membrane.

In the positron beam method, the measurement band in the depth direction from the sample surface is regulated on the basis of the amount of energy of the incident positron beam. As the energy is increased, a proportion that is deeper from the sample surface is included in the measurement band, but the depth is dependent on the density of the sample. To measure the separation functional layer of a nanofiltration membrane, when a positron beam enters usually with an energy of about 1 keV, a band of about 50 to 150 nm from the sample surface is measured. In the case of a separation functional layer having a thickness of about 150 to 300 nm, particularly the central part in the separation functional layer can be selectively measured.

A positron and an electron binds with their mutual coulombic force and generate positronium Ps, which is a neutral hydrogen-like atom. Ps has para-positronium, p-Ps, and ortho-positronium, o-Ps, depending on whether the spins of the positrons and the electrons are antiparallel or parallel, or the like, and the para-positronium and the ortho-positronium are generated at a ratio of 1:3 according to the spin statistics theorem. Their respective average lifetimes are 125 p for the p-Ps and 140 ps for the o-Ps. However, in a substance in an aggregated state, the o-Ps is superposed with an electron that is different from what is bound to itself, and has an increased probability of causing an annihilation called pick-off annihilation. As a result, the average lifetime of the o-Ps is shortened to a few nanoseconds. The annihilation of the o-Ps in an insulating material is caused by the overlapping of an o-Ps with an electron present on the pore walls in the substance, and as the pore size is smaller, the annihilation rate is accelerated. That is, the annihilation lifetime of an o-Ps can be correlated to the pore diameter in an insulating material.

The annihilation lifetime τ based on the pick-off annihilation of o-Ps can be obtained in an analysis made by dividing a positron annihilation lifetime curve measured by a positron annihilation lifetime spectroscopy, into four components by a non-linear least squares program, POSITRONFIT (the details are described in, for example, P. Kirkegaard, et al., Computer Physic Communications, Vol. 3, p. 240, North Holland Publishing Company (1972)), specifically from the analysis results for the fourth component.

The average pore radius R in the separation functional layer of the nanofiltration membrane is a value determined from the following formula (1), by using the positron annihilation lifetime τ. The formula (1) represents the relationship in the case of assuming that the o-Ps is present in a pore having a radius R in an electron layer having a thickness of ΔR, and ΔR is empirically determined to be 0.166 nm (the details are described in Nakanishi, et al., Journal of Polymer Science Part B: Polymer Physics, Vol. 27, p. 1419, John Wiley & Sons, Incorporated (1989)).

[Expression 1]
[Expression 1]

$$\tau^{-1} = 2\left[1 - \frac{R}{R+\Delta R} + \frac{1}{2\pi}\sin\left(\frac{2\pi R}{R+\Delta R}\right)\right] \quad (1)$$

Upon the expression of the performance of a separation membrane, use is made of not only the removal rates described above, but also the permeation performance, which is in a tradeoff relationship with the removal rates. For example, in a separation membrane having equal removal rates and high permeation performance, the time required for the separation operation is shortened, which is preferable. A separation membrane which exhibits a permeation performance of 0.5 m$^3$/m$^2$d or greater when a 500 ppm aqueous glucose solution at pH 6.5 at 25° C. is permeated therethrough at an operation pressure of 0.5 MPa, is used with preference. A separation membrane exhibiting a permeation performance of 0.7 m$^3$/m$^2$d or greater is more preferable because the separation operation can be performed in a shorter time.

Separation membranes can be carefully selected and connected together for use according to necessity to control the water quality. In regard to the selection and connection of the separation membranes, if at least one separation membrane that exhibits a glucose removal rate and an isopropyl alcohol removal rate in the ranges described above is used, fermentation inhibitors can be efficiently removed. For example, first, it is acceptable to carry out a treatment roughly by using a separation membrane having a low removal rate for fermentation inhibitors but having high permeation performance, and then to carry out a treatment for enhancing water quality by using a separation membrane having low permeation performance but having a high removal rate for fermentation inhibitors. Such selection and connection of separation membranes is used with preference in the case where the concentration of the monosaccharide and/or oligosaccharide of a pentose and/or a hexose as well as the concentration of the fermentation inhibitor are all low, because concentration and removal of the fermentation inhibitor can be carried out simultaneously.

The shape of the separation membrane is not particularly limited as long as the membrane is capable of treating a polysaccharide-based biomass, and can be selected for use from a smooth membrane shape, a hollow fiber membrane shape, a pleated membrane shape, a tubular membrane shape, and the like. Particularly, a so-called spiral type element, which is produced by processing a smooth membrane into an envelop shape, and rolling the membrane into a whirled shape together with various members such as a net, is used with preference, because the membrane area can be enlarged.

The separation membrane may be disposed from a point where a fermentation inhibitor is generated, to a point where the fermentation inhibitor is transported to the steps which are adversely affected by the fermentation inhibitor, such as saccharification making use of an enzyme, and separation processes, so that the fermentation inhibitor may be removed to the extent that the fermentation inhibitor does not adversely affect the subsequent processes. Furthermore, to control the water quality, the method of supplying raw water to the separation membrane can also be freely designed, such that the recovery rate is modified, or a part of the raw water is circulated. For example, the method of supplying may also be modified based on the type of the polysaccharide-based biomass.

As such, the treatment of a polysaccharide-based biomass with the use of a separation membrane has a high degree of freedom in design, and thus even when various polysaccharide-based biomasses are used as starting materials, the fermentation inhibitor can be removed to the extent that fermentation inhibitors do not adversely affect the subsequent processes.

Furthermore, to remove a fermentation inhibitor from a solution containing a monosaccharide and/or an oligosaccharide of a pentose and/or a hexose, by using a separation membrane exhibiting a glucose removal rate and an isopropyl alcohol removal rate in the ranges mentioned above, the monosaccharide and/or oligosaccharide of a pentose and/or a hexose is more concentrated than the fermentation inhibitor, and is recovered to a brine side. That is, when a separation membrane exhibiting a glucose removal rate and an isopropyl alcohol removal rate in the ranges described above is used, a situation may occur where concentration of a monosaccharide and/or an oligosaccharide of a pentose and/or a hexose can be carried out simultaneously while a fermentation inhibitor is removed. Thus, the separation membrane can be particularly suitably used in a solution having a low concentration of a monosaccharide and/or an oligosaccharide of a pentose and/or a hexose. As a result, a conventional method which requires two steps of a step for concentrating a monosaccharide and/or an oligosaccharide of a pentose and/or a hexose, and a step for removing a fermentation inhibitor, can be shortened into a single step, or the burden of the concentration step can be reduced.

Hereinafter, our methods will be described by way of specific Examples, but this disclosure is not intended to be limited by these Examples.

EXAMPLES

The measurements in Examples and Comparative Examples were carried out as follows. Furthermore, separation membranes A to G used in the Examples and Comparative Examples were produced as follows.

In Examples 1 to 8 and Comparative Examples 1 and 2, the following model aqueous solution was prepared and supplied to various separation membranes, to evaluate whether a fermentation inhibitor can be removed from a monosaccharide and/or an oligosaccharide of a pentose and/or a hexose. That is, glucose and sucrose were used as the monosaccharide and/or oligosaccharide of a pentose and/or a hexose, and furfural, 5-hydroxymethylfurfural and vanillin were used as fermentation inhibitors. A model aqueous solution was prepared by dissolving each of the substances in water to a concentration of 500 ppm.

In Example 9, glucose was used as the monosaccharide and/or oligosaccharide of a pentose and/or a hexose, and furfural, 5-hydroxymethylfurfural and vanillin were used as fermentation inhibitors, so as to investigate the effect of the fermentation inhibitor concentration on the growth rate of a colon bacillus and yeast.

(Isopropyl Alcohol Removal Rate)

An evaluation was made by comparing the isopropyl alcohol concentrations in the permeation water and the source water, which were obtained when a 500 ppm aqueous isopropyl alcohol solution adjusted to pH 6.5 and a temperature of 25° C. was supplied to a separation membrane at an operation pressure of 0.5 MPa. That is, calculation was performed by the formula: isopropyl alcohol removal rate (%)=100×(1−(isopropyl alcohol concentration in permeation water/isopropyl alcohol concentration in source water)). The isopropyl alcohol concentration was determined by conventional gas chromatography analysis.

(Glucose Removal Rate)

An evaluation was made by comparing the glucose concentrations in the permeation water and the source water, which were obtained when a 500 ppm aqueous glucose solution adjusted to pH 6.5 and a temperature of 25° C. was supplied to a separation membrane at an operation pressure of 0.5 MPa. That is, calculation was performed by the formula: glucose removal rate (%)=100×(1−(glucose concentration in permeation water/glucose concentration in source water)). The glucose concentration was determined by using a refractometer (RID-6A, manufactured by Shimadzu Corp.).

(Permeation Performance)

The amount of permeation water ($m^3$) per unit time (d) and unit area ($m^2$) obtained when a 500 ppm aqueous glucose solution adjusted to pH 6.5 at a temperature of 25° C. was supplied to a separation membrane at an operation pressure of 0.5 MPa, was measured, and the permeation performance ($m^3/m^2d$) was calculated.

(Positron Annihilation Lifetime Spectroscopy According to Positron Beam Method)

To perform positron annihilation lifetime spectroscopy without particularly processing the separation functional layer of a separation membrane, the analysis may be made by using a positron beam method as follows. That is, a measurement sample dried under reduced pressure at room temperature and cut to a size of 1.5 cm×1.5 cm, was measured with thin film corresponding positron annihilation lifetime measuring apparatus having a positron beam generating apparatus (the details of the apparatus are described in, for example, Radiation Physics and Chemistry, vol. 58, p. 603, Pergamon Press (2000)), with a beam intensity of 1 keV, in a vacuum at room temperature, at a total count number of 5,000,000 by means of a scintillation counter made of barium difluoride using a photomultiplier tube. An interpretation is performed with POSITRONFIT. From the average lifetime τ of the fourth component obtained by the interpretation, the average pore radius R, average pore volume V, relative intensity I, and amount pores V×I can be analyzed.

(Production of Polysulfone Supporting Film)

The polysulfone supporting film was produced by the following technique. That is, a wet non-woven cloth of a mixed fabric of polyester fibers respectively having a single yarn fineness of 0.5 and 1.5 decitex, the non-woven cloth having a size of 30 cm in length and 20 cm in width, an air permeability of 0.7 cm$^3$/cm$^2$. second and an average pore diameter of 7 μm or less, was fixed onto a glass plate. A solution of polysulfone at a concentration 15 wt % in a dimethylformamide (DMF) solvent (2.5 Poise: 20° C.) was cast on the wet non-woven cloth to a total thickness of 200 μm, and the assembly was immediately submerged in water. Thus, a polysulfone supporting film was obtained.

(Production of Separation Membrane A)

The polysulfone supporting film was immersed for 2 minutes in an aqueous solution containing 2.0 wt % of m-phenylenediamine and 2.0 wt % of ϵ-caprolactam, and then a solution prepared by dissolving trimesic acid chloride in decane to a concentration of 0.1 wt % was applied thereon to a proportion of 160 cm$^3$/m$^2$. Then, excess solution was removed, and thus a separation membrane was obtained. The separation membrane thus obtained was treated for 2 minutes at room temperature with an aqueous solution containing 0.07 wt % of sodium nitrite and 0.1 wt % of concentrated sulfuric acid, subsequently was immediately washed with water, and was stored at room temperature. Thus, a separation membrane A was obtained.

(Production of Separation Membrane B)

20.0 g of ethanol and 10.8 g of glycerin were added to a beaker, and while the mixture was vigorously stirred, 20.0 g of tetra-n-butoxytitanium was added thereto. After 5 minutes, while the gel thus obtained was stirred with a glass rod, 6.0 g of 28% aqueous ammonia was added thereto. After the gel turned into a cloudy solution form, the gel was further stirred for 2 hours with a stirrer. The cloudy solution thus obtained was subjected to a centrifuge (2,500 rpm, 3 minutes). Precipitated white solids were made into a cloudy solution again with ethanol, and the cloudy solution was subjected to a centrifuge (2,500 rpm, 3 minutes). Precipitated white solids were recovered. The white solids thus obtained were dried in a vacuum at normal temperature, and was further dried in a vacuum at 120° C. for 3 hours. Thus, a white solid in a powder form was obtained.

The white solid in a powder form thus obtained was prepared into a dilute hydrochloric acid solution (whit solid/water/1 N hydrochloric acid=1/5.5/3.5 wt %), and the solution was applied on the polysulfone supporting film. Liquid droplets at the surface were removed by nitrogen blowing, and then the assembly was dried for one hour with a hot air dryer at 90° C. Thus, a separation membrane B was obtained.

(Production of Separation Membrane C)

The polysulfone supporting film was immersed for 2 minutes in an aqueous solution containing 2.0 wt % of m-phenylenediamine and 2.0 wt % of s-caprolactam, and then a solution prepared by dissolving trimesic acid chloride in decane to a concentration of 0.1 wt % was applied thereon to a proportion of 160 cm$^3$/m$^2$. Then, excess solution was removed, and thus a separation membrane was obtained. The separation membrane thus obtained was treated for 2 minutes at room temperature with an aqueous solution containing 7 wt % of sodium nitrite and 0.1 wt % of concentrated sulfuric acid, subsequently was immediately washed with water, and was stored at room temperature. Thus, a separation membrane C was obtained.

(Production of Separation Membrane D)

The polysulfone supporting film was immersed for 2 minutes in an aqueous solution containing 2.0 wt % of m-phenylenediamine and 2.0 wt % of s-caprolactam, and then a solution prepared by dissolving trimesic acid chloride in decane to a concentration of 0.1 wt % was applied thereon to a proportion of 160 cm$^3$/m$^2$. Then, excess solution was removed, and thus a separation membrane was obtained. The separation membrane thus obtained was treated for 60 minutes at room temperature with an aqueous solution containing 0.07 wt % of sodium nitrite and 0.1 wt % of concentrated sulfuric acid, subsequently was immediately washed with water, and was stored at room temperature. Thus, a separation membrane D was obtained.

(Production of Separation Membrane E)

The polysulfone supporting film was immersed for 1 minute in an aqueous solution containing 2.0 wt % of m-phenylenediamine, and then a solution prepared by dissolving trimesic acid chloride in decane to a concentration of 0.1 wt % was applied thereon to a proportion of 160 cm$^3$/m$^2$. Then, excess solution was removed, and the assembly was immersed in a 0.2 wt % aqueous solution of sodium carbonate for 5 minutes. The separation membrane thus obtained was immersed for 2 minutes in an aqueous solution of potassium peroxymonosulfate adjusted to a concentration of 1.0 wt % and pH 6, subsequently was washed immediately with water, and was stored at room temperature. Thus, a separation membrane E was obtained.

(Production of Separation Membrane F)

The polysulfone supporting film was coated with an aqueous solution containing 1.0 wt % of piperazine, 0.2 wt % of 1,3-bis(4-piperidyl)-propane, 0.5 wt % of sodium dodecyl sulfate, and 1.0 wt % of trisodium phosphate, and was dried with air at room temperature for 2 minutes. Subsequently, a solution prepared by dissolving a mixture of isophthalic acid chloride and trimesic acid chloride (weight ratio 2:1) in decane at 1.0 wt %, was applied thereon to a proportion of 160 cm$^3$/m$^2$, and the assembly was heat treated for 5 minutes with hot air at 100° C. The assembly was then washed immediately with water and was stored at room temperature. Thus, a separation membrane F was obtained.

(Production of Separation Membrane G)

The polysulfone supporting film was coated with an aqueous solution containing 1.0 wt % of piperazine, 0.2 wt % of 1,3-bis(4-piperidyl)-propane, 2.0 wt % of sodium dodecyl sulfate, and 1.0 wt % of trisodium phosphate, and was dried with hot air at 80° C. for 30 seconds. Subsequently, a solution prepared by dissolving a mixture of isophthalic acid chloride and trimesic acid chloride (weight ratio 1:1) in decane at 0.5 wt %, was applied thereon to a proportion of 160 cm$^3$/m$^2$, and the assembly was heat treated for 5 minutes with hot air at 100° C. The assembly was then washed immediately with water and was stored at room temperature. Thus, a separation membrane G was obtained.

Example 1

UTC-60 (crosslinked polyamide nanofiltration (NF) membrane manufactured by Toray Industries, Inc.) was used as a separation membrane to evaluate the isopropyl alcohol removal rate, glucose removal rate, and permeation performance. UTC-60 had an isopropyl alcohol removal rate of 35%, a glucose removal rate of 95%, and a permeation performance of 1.1 m$^3$/m$^2$d, and the difference between the glucose removal rate and the isopropyl alcohol removal rate was 60%. Furthermore, the average pore radius of UTC-60 as measured by a positron annihilation lifetime spectroscopy was from 2.5 nm to 3.5 nm.

A model aqueous solution adjusted to a temperature of 25° C. and at pH 6.5 was supplied at an operation pressure of 0.5 MPa, and the glucose concentrations, sucrose concentrations, furfural concentrations, 5-hydroxymethylfurfural concentrations and vanillin concentrations of the permeation water and the source water were measured using a refractometer (RID-6A, manufactured by Shimadzu Corp.) or an ultraviolet-visible absorptiometer (UV VISIBLE SPECTROPHOTOMETER 2450, manufactured by Shimadzu Corp.), and the respective removal rates were determined. The results are summarized in Table 1. As it can be seen from Table 1, since UTC-60 had high glucose and sucrose removal rates, and low furfural, 5-hydroxymethylfurfural and vanillin removal rates, it was found that the membrane was capable of removing fermentation inhibitors from a monosaccharide and/or an oligosaccharide of a pentose and/or a hexose.

Example 2

The operation was performed in the same manner as in Example 1, except that UTC-20 (crosslinked polyamide nanofiltration (NF) membrane manufactured by Toray Industries, Inc.) was used as a separation membrane. UTC-20 had an isopropyl alcohol removal rate of 30%, a glucose removal rate of 84%, and a permeation performance of 0.8 m$^3$/m$^2$d, and the difference between the glucose removal rate and the isopropyl alcohol removal rate was 54%. Furthermore, the average pore radius of UTC-20 as measured by a positron annihilation lifetime spectroscopy was from 3.5 nm to 4.0 nm.

Furthermore, the results of evaluation performed using the model aqueous solution, are summarized in Table 1. As it can be seen from Table 1, since UTC-20 had high glucose and sucrose removal rates, and low furfural, 5-hydroxymethylfurfural and vanillin removal rates, it was found that the membrane was capable of removing fermentation inhibitors from a monosaccharide and/or an oligosaccharide of a pentose and/or a hexose.

Example 3

The operation was performed in the same manner as in Example 1, except that the separation membrane A was used as a separation membrane. The separation membrane A had an isopropyl alcohol removal rate of 70%, a glucose removal rate of 99.5%, and a permeation performance of 1.3 m$^3$/m$^2$d, and the difference between the glucose removal rate and the isopropyl alcohol removal rate was 29.5%. Furthermore, the average pore radius of the separation membrane A as measured by a positron annihilation lifetime spectroscopy was from 0.8 nm to 1.0 nm.

Furthermore, the results of evaluation performed using the model aqueous solution, are summarized in Table 1. As it can be seen from Table 1, the separation membrane A had high glucose and sucrose removal rates, and it was found that there was almost no outflow of glucose and sucrose into the permeation side. On the other hand, since the removal rates for furfural, 5-hydroxymethylfurfural and vanillin were lower compared with the glucose and sucrose removal rates, it was found that the membrane was capable of removing fermentation inhibitors from a monosaccharide and/or an oligosaccharide of a pentose and/or a hexose.

Example 4

The operation was performed in the same manner as in Example 1, except that the separation membrane C was used as a separation membrane. The separation membrane C had an isopropyl alcohol removal rate of 62%, a glucose removal rate of 99%, and a permeation performance of 1.6 m$^3$/m$^2$d, and the difference between the glucose removal rate and the isopropyl alcohol removal rate was 37%. Furthermore, the average pore radius of the separation membrane A as measured by a positron annihilation lifetime spectroscopy was from 1.0 nm to 1.5 nm.

Furthermore, the results of evaluation performed using the model aqueous solution, are summarized in Table 1. As it can be seen from Table 1, the separation membrane A had high glucose and sucrose removal rates, and it was found that there was almost no outflow of glucose and sucrose into the permeation side. On the other hand, since the removal rates for furfural, 5-hydroxymethylfurfural and vanillin were lower compared with the glucose and sucrose removal rates, it was found that the membrane was capable of removing fermentation inhibitors from a monosaccharide and/or an oligosaccharide of a pentose and/or a hexose.

Example 5

The operation was performed in the same manner as in Example 1, except that the separation membrane D was used as a separation membrane. The separation membrane D had an isopropyl alcohol removal rate of 60%, a glucose removal rate of 98.5%, and a permeation performance of 1.7 m$^3$/m$^2$d, and the difference between the glucose removal rate and the isopropyl alcohol removal rate was 38.5%. Furthermore, the average pore radius of the separation membrane A as measured by a positron annihilation lifetime spectroscopy was from 1.0 nm to 1.7 nm.

Furthermore, the results of evaluation performed using the model aqueous solution, are summarized in Table 1. As it can be seen from Table 1, the separation membrane A had high glucose and sucrose removal rates, and it was found that there was almost no outflow of glucose and sucrose into the permeation side. On the other hand, since the removal rates for furfural, 5-hydroxymethylfurfural and vanillin were lower compared with the glucose and sucrose removal rates, it was found that the membrane was capable of removing fermentation inhibitors from a monosaccharide and/or an oligosaccharide of a pentose and/or a hexose.

Example 6

The operation was performed in the same manner as in Example 1, except that the separation membrane E was used as a separation membrane. The separation membrane E had an isopropyl alcohol removal rate of 75%, a glucose removal rate of 98%, and a permeation performance of 0.9 m$^3$/m$^2$d, and the difference between the glucose removal rate and the isopropyl alcohol removal rate was 23%. Furthermore, the average pore radius of the separation membrane A as measured by a positron annihilation lifetime spectroscopy was from 0.8 nm to 1.5 nm.

Furthermore, the results of evaluation performed using the model aqueous solution, are summarized in Table 1. As it can be seen from Table 1, the separation membrane A had high glucose and sucrose removal rates, and it was found that there was almost no outflow of glucose and sucrose into the permeation side. On the other hand, since the removal rates for furfural, 5-hydroxymethylfurfural and vanillin were lower compared with the glucose and sucrose removal rates, it was found that the membrane was capable of removing fermentation inhibitors from a monosaccharide and/or an oligosaccharide of a pentose and/or a hexose.

Example 7

The operation was performed in the same manner as in Example 1, except that the separation membrane F was used as a separation membrane. The separation membrane F had an isopropyl alcohol removal rate of 32%, a glucose removal rate of 90%, and a permeation performance of 1.5 $m^3/m^2d$, and the difference between the glucose removal rate and the isopropyl alcohol removal rate was 58%. Furthermore, the average pore radius of the separation membrane A as measured by a positron annihilation lifetime spectroscopy was from 2.5 nm to 3.5 nm.

Furthermore, the results of evaluation performed using the model aqueous solution, are summarized in Table 1. As it can be seen from Table 1, the separation membrane A had high glucose and sucrose removal rates, and it was found that there was almost no outflow of glucose and sucrose into the permeation side. On the other hand, since the removal rates for furfural, 5-hydroxymethylfurfural and vanillin were lower compared with the glucose and sucrose removal rates, it was found that the membrane was capable of removing fermentation inhibitors from a monosaccharide and/or an oligosaccharide of a pentose and/or a hexose.

Example 8

The operation was performed in the same manner as in Example 1, except that the separation membrane G was used as a separation membrane. The separation membrane G had an isopropyl alcohol removal rate of 36%, a glucose removal rate of 95%, and a permeation performance of 1.3 $m^3/m^2d$, and the difference between the glucose removal rate and the isopropyl alcohol removal rate was 59%. Furthermore, the average pore radius of the separation membrane A as measured by a positron annihilation lifetime spectroscopy was from 2.5 nm to 3.5 nm.

Furthermore, the results of evaluation performed using the model aqueous solution, are summarized in Table 1. As it can be seen from Table 1, the separation membrane A had high glucose and sucrose removal rates, and it was found that there was almost no outflow of glucose and sucrose into the permeation side. On the other hand, since the removal rates for furfural, 5-hydroxymethylfurfural and vanillin were lower compared with the glucose and sucrose removal rates, it was found that the membrane was capable of removing fermentation inhibitors from a monosaccharide and/or an oligosaccharide of a pentose and/or a hexose.

Comparative Example 1

The operation was performed in the same manner as in Example 1, except that UTC-70U (crosslinked polyamide reverse osmosis (RO) membrane manufactured by Toray Industries, Inc.) was used as a separation membrane. UTC-70U had an isopropyl alcohol removal rate of 96.2%, a glucose removal rate of 99.9%, and a permeation performance of 0.7 $m^3/m^2d$, and the difference between the glucose removal rate and the isopropyl alcohol removal rate was only 3.7%. Furthermore, the average pore radius of UTC-70U as measured by a positron annihilation lifetime spectroscopy was from 0.25 nm to 0.35 nm.

Furthermore, the results of evaluation performed using the model aqueous solution, are summarized in Table 1. As it can be seen from Table 1, UTC-70U had high glucose and sucrose removal rates, but the removal rates for furfural, 5-hydroxymethylfurfural and vanillin were also high. Therefore, it was found that it is difficult for the membrane to remove fermentation inhibitors from a monosaccharide and/or an oligosaccharide of a pentose and/or a hexose.

Comparative Example 2

The operation was performed in the same manner as in Example 1, except that the separation membrane B was used as a separation membrane. The separation membrane B had an isopropyl alcohol removal rate of 1%, a glucose removal rate of 29%, and a permeation performance of 2.0 $m^3/m^2d$, and the difference between the glucose removal rate and the isopropyl alcohol removal rate was 28%. Furthermore, probably because the pore diameter of the separation membrane B was too large, the average pore radius of the separation membrane B could not be measured by a positron annihilation lifetime spectroscopy.

Furthermore, the results of evaluation performed using the model aqueous solution, are summarized in Table 1. As it can be seen from Table 1, since the separation membrane B had low glucose and sucrose removal rates, it was found that a monosaccharide and/or an oligosaccharide of a pentose and/or a hexose has flowed out.

Example 9

A spiral type element SU-620 (manufactured by Toray Industries, Inc., membrane area 28 $m^2$) containing the UTC-60 used in Example 1 as a separation membrane, was purchased, and this spiral type element SU-620 was used to treat 100 L of a solution (1) containing 1.0 wt % of glucose, 1000 ppm of furfural, 1000 ppm of 5-hydroxymethylfurfural and 1000 ppm of vanillin at a recovery rate of 60%. As a result, 40 L of a solution (2) containing 2.4 wt % of glucose, 1150 ppm of furfural, 1200 ppm of 5-hydroxymethylfurfural and 1150 ppm of vanillin was obtained. Water was added to the solution (2) to adjust the glucose concentration to 1.0 wt %, and thus a solution (3) containing 480 ppm of furfural, 500 ppm of 5-hydroxymethylfurfural and 480 ppm of vanillin was obtained.

The solution (3) was treated again using SU-620 at a recovery rate of 60%, and as a result, a solution (4) containing 2.4 wt % of glucose, 550 ppm of furfural, 600 ppm of 5-hydroxymethylfurfural and 550 ppm of vanillin was obtained. Water was added to the solution (4) to adjust the glucose concentration to 1.0 wt %, and thus a solution (5) containing 230 ppm of furfural, 250 ppm of 5-hydroxymethylfurfural and 230 ppm of vanillin was obtained.

The solution (5) was further treated using SU-620 at a recovery rate of 60%, and as a result, a solution (6) containing 2.4 wt % of glucose, 290 ppm of furfural, 310 ppm of 5-hydroxymethylfurfural and 290 ppm of vanillin was obtained. Water was added to the solution (6) to adjust the glucose concentration to 1.0 wt %, and thus a solution (7) containing 120 ppm of furfural, 130 ppm of 5-hydroxymethylfurfural and 120 ppm of vanillin was obtained.

A solution (0) which contained 1.0 wt % of glucose only and did not contain furfural, 5-hydroxymethylfurfural and vanillin was prepared.

The reason for adjusting the glucose concentration of each solution to 1.0 wt % was to evaluate the growth rates of colon bacillus and yeast that will be described below, at an equal glucose concentration.

The measurement of the concentrations of glucose, furfural, 5-hydroxymethylfurfural and vanillin was carried out using high performance liquid chromatography. That is, a liquid chromatographic liquid transport unit (LC-10AD, manufactured by Shimadzu Corp.) was used, and a commercially available reverse phase column (ODS column) and a commercially available sugar separation column (CAPCELL PAK NH2SG) were used to perform separation. The respective concentrations were measured using a refractometer (RID-6A, manufactured by Shimadzu Corp.) or an ultraviolet visible absorptiometer (SPD-10A, manufactured by Shimadzu Corp.) as detectors.

The solutions (0), (1), (3) and (7) were used as substrates, and the growth rates of colon bacillus and yeast were evaluated. Thus, the effect of the concentrations of furfural, 5-hydroxymethylfurfural and vanillin on fermentation was investigated.

The growth rates of colon bacillus and yeast were evaluated by the following method.

A colon bacillus (*Escherichia coli* strain W3110) and yeast (*Saccharomyces cerevisiae* NBRC2260) were used as the bacteria under test. The colon bacillus and the yeast were subjected to shaken culture (whole culture) at 30° C. for 24 hours, using LB medium (1% trypton, 0.5% yeast extract and 1% sodium chloride) for the colon bacillus and using YPD medium (2% trypton, 1% yeast extract and 2% glucose) for the yeast. As evaluation media, evaluation media (0), (1), (3) and (7) were prepared by adding corn sleep liquor to the solutions (0), (1), (3) and (7) to obtain a final concentration of 5%, and adjusting the solutions to pH 7. To 50 mL each of these evaluation media ((0), (1), (3) and (7)), 3 mL of the culture liquor obtained after whole culture was added, and the mixtures were subjected to shaking culture at 30° C. for 24 hours. The growth amounts of the colon bacillus and yeast after 24 hours of culture were calculated by measuring the absorbance at 600 nm (OD600 value). When the OD600 value of the colon bacillus or yeast after 24 hours in the evaluation medium (0) was taken as 100, the respective growth rates in the evaluation media (1), (3) and (7) are summarized in Table 2.

Particularly, the evaluation medium (7) containing 120 to 130 ppm of furfural 5-hydroxymethylfurfural and vanillin concentrations, exhibited growth rates of the colon bacillus and yeast that were almost equal to the growth rates obtainable in the evaluation medium (0) which did not contain furfural, 5-hydroxymethylfurfural and vanillin, and thus a remarkable effect of removing fermentation inhibitors was observed.

TABLE 1-1

|  | Example 1 | Example 2 | Example 3 | Example 4 | Example 5 |
|---|---|---|---|---|---|
| Type of separation membrane | UTC-60 | UTC-20 | Separation membrane A | Separation membrane C | Separation membrane D |
| Isopropyl alcohol removal rate (%) | 35 | 30 | 70 | 62 | 60 |
| Glucose removal rate (%) | 95 | 84 | 99.5 | 99 | 98.5 |
| Glucose removal rate (%) − Isopropyl alcohol removal rate (%) | 60 | 54 | 29.5 | 37 | 38.5 |
| Permeation performance (m$^2$/m$^2$d) | 1.1 | 0.8 | 1.3 | 1.6 | 1.7 |
| Model aqueous solution — Glucose removal rate (%) | 92 | 80 | 99 | 98.5 | 97 |
| Model aqueous solution — Sucrose removal rate (%) | 99 | 88 | 99.9 | 99.9 | 99 |
| Model aqueous solution — Furfural removal rate (%) | 9 | 10 | 90 | 83 | 80 |
| Model aqueous solution — 5-Hydroxymethylfurfural removal rate (%) | 13 | 12 | 93 | 89 | 86 |
| Model aqueous solution — Vanillin removal rate (%) | 10 | 10 | 90 | 84 | 82 |
| Average pore radius based on positron annihilation lifetime measurement method (nm) | 2.5-3.5 | 3.5-4.0 | 0.8-1.0 | 1.0-1.5 | 1.0-1.7 |

TABLE 1-2

|  | Example 6 | Example 7 | Example 8 | Comparative Example 1 | Comparative Example 2 |
|---|---|---|---|---|---|
| Type of separation membrane | Separation membrane E | Separation membrane F | Separation membrane G | UTC-70U | Separation membrane B |
| Isopropyl alcohol removal rate (%) | 75 | 32 | 36 | 96.2 | 1 |
| Glucose removal rate (%) | 98 | 90 | 95 | 99.9 | 29 |
| Glucose removal rate (%) − Isopropyl alcohol removal rate (%) | 23 | 58 | 59 | 3.7 | 28 |
| Permeation performance (m$^2$/m$^2$d) | 0.9 | 1.5 | 1.3 | 0.7 | 2 |
| Model aqueous solution — Glucose removal rate (%) | 97 | 87 | 89 | 99.9 | 28 |
| Model aqueous solution — Sucrose removal rate (%) | 99 | 95 | 97 | 99.9 | 33 |
| Model aqueous solution — Furfural removal rate (%) | 86 | 7 | 8 | 99.9 | 0 |
| Model aqueous solution — 5-Hydroxymethylfurfural removal rate (%) | 90 | 8 | 10 | 99.9 | 0 |
| Model aqueous solution — Vanillin removal rate (%) | 90 | 8 | 11 | 99.9 | 0 |
| Average pore radius based on positron annihilation lifetime measurement method (nm) | 0.8-1.5 | 2.5-3.5 | 2.5-3.5 | 0.25-0.35 | Unmeasurable |

TABLE 2

| Solution | Evaluation medium | | | |
| --- | --- | --- | --- | --- |
| | (1) (1) | (3) (3) | (7) (7) | (0) (0) |
| Glucose concentration (wt %) | 1.0 | 1.0 | 1.0 | 1.0 |
| Furfural concentration (ppm) | 1000 | 480 | 120 | 0 |
| 5-Hydroxymethylfurfural concentration (ppm) | 1000 | 500 | 130 | 0 |
| Vanillin concentration (ppm) | 1000 | 480 | 120 | 0 |
| Growth rate of colon bacillus (—) | 5 | 18 | 92 | 100 |
| Growth rate of yeast (—) | 23 | 62 | 96 | 100 |

Industrial Applicability

The method of producing a compound originating from a polysaccharide-based biomass can be suitably used when saccharides are produced by using a polysaccharide-based biomass as a starting material, and when the saccharides thus obtained are converted into chemicals via fermentation.

The invention claimed is:

1. A method of producing a compound originating from a polysaccharide-based biomass comprising:

at least one of a saccharification step that produces a sugar solution containing 1) a monosaccharide and an oligosaccharide or 2) a monosaccharide or 3) an oligosaccharide from a product obtainable by hydrolyzing the polysaccharide-based biomass;

a fermentation step that ferments the sugar solution containing 1) the monosaccharide and oligosaccharide or 2) the monosaccharide or 3) the oligosaccharide originating from the polysaccharide-based biomass; and a treatment step that removes a fermentation inhibitor with a nanofiltration membrane comprising at least one selected from the group consisting of a cross-linked piperazine polyamide nanofiltration membrane, a cellulose acetate nanofiltration membrane and a polyamide nanofiltration membrane, having a glucose removal rate and an isopropyl alcohol removal rate which simultaneously satisfy relationships (I) and (II) when a 500 parts per million (ppm) aqueous glucose solution at pH 6.5 at 25° C. and a 500 ppm aqueous isopropyl alcohol solution at pH 6.5 at 25° C. are respectively permeated through the membrane at an operation pressure of 0.5 MegaPascals (MPa), 1) prior to the saccharification step and in the step prior to the fermentation step or 2)prior to the saccharification step or 3) in the step prior to the fermentation step:

Glucose removal rate≥80% (I)

Glucose removal rate−Isopropyl alcohol removal rate≥20% (II).

2. The method according to claim 1, wherein said nanofiltration membrane is a composite membrane comprising polyamide as a functional layer on a polysulfone supporting film.

3. The method according to claim 1, wherein the treatment step that removes the fermentation inhibitor with the nanofiltration membrane facilitates removal of the fermentation inhibitor and concurrent concentration of any one of cellulose, a hemicellulose, a monosaccharide and an oligosaccharide.

4. The method according to claim 2, wherein the treatment step that removes the fermentation inhibitor with the nanofiltration membrane facilitates removal of the fermentation inhibitor and concurrent concentration of any one of cellulose, a hemicellulose, a monosaccharide and an oligosaccharide.

5. The method according to claim 1, further comprising a treatment step that concentrates the compound with a reverse osmosis membrane performed after the treatment step that removes the fermentation inhibitor and before the fermentation step.

6. The method according to claim 2, further comprising a treatment step that concentrates the compound with a reverse osmosis membrane performed after the treatment step that removes the fermentation inhibitor and before the fermentation step.

7. The method according to claim 1, wherein the treatment step that removes the fermentation inhibitor is carried out until content of the fermentation inhibitor in the sugar solution obtainable immediately before the fermentation step reaches 500 ppm or less.

8. The method according to claim 2, wherein the treatment step that removes the fermentation inhibitor is carried out until content of the fermentation inhibitor in the sugar solution obtainable immediately before the fermentation step reaches 500 ppm or less.

9. The method according to claim 1, wherein the nanofiltration membrane has pores with an average pore radius as measured by a positron annihilation lifetime spectroscopy of 0.8 nm to 4.0 nm.

10. The method according to claim 2, wherein the nanofiltration membrane has pores with an average pore radius as measured by a positron annihilation lifetime spectroscopy of 0.8 nm to 4.0 nm.

11. The method according to claim 9, wherein average pore radius is 2.5 nm to 4.0 nm.

12. The method according to claim 10, wherein average pore radius is 2.5 nm to 4.0 nm.

* * * * *